(12) United States Patent
Mellor et al.

(10) Patent No.: US 7,227,017 B2
(45) Date of Patent: Jun. 5, 2007

(54) PROCESS FOR THE PREPARATION OF PHOSPHOROTHIOATE OLIGONUCLEOTIDES

(75) Inventors: Ben James Mellor, Grangemouth (GB); Donald Alfred Wellings, Blackley (GB); Mark Edward Douglas, Blackley (GB)

(73) Assignee: Avecia Limited, Manchester (GB)

( * ) Notice: Subject to any disclaimer, the term of this patent is extended or adjusted under 35 U.S.C. 154(b) by 571 days.

(21) Appl. No.: 10/454,841

(22) Filed: Jun. 5, 2003

(65) Prior Publication Data

US 2003/0229221 A1    Dec. 11, 2003

Related U.S. Application Data

(63) Continuation-in-part of application No. PCT/GB01/05338, filed on Dec. 3, 2001, which is a continuation-in-part of application No. 09/740,031, filed on Dec. 20, 2000, now Pat. No. 6,768,005.

(30) Foreign Application Priority Data

May 12, 2000    (GB) ................................. 0029610.3

(51) Int. Cl.
  *C07H 21/00*    (2006.01)
(52) U.S. Cl. ............................. 536/25.34; 536/25.33; 536/25.3
(58) Field of Classification Search ............... 536/25.3, 536/25.33, 25.34
  See application file for complete search history.

(56) References Cited

U.S. PATENT DOCUMENTS

| 4,458,066 | A | * | 7/1984 | Caruthers et al. ......... 536/25.34 |
| 4,500,707 | A | * | 2/1985 | Caruthers et al. ......... 536/25.34 |
| 4,753,985 | A | | 6/1988 | Rosevear et al. |
| 4,795,700 | A | | 1/1989 | Dervan et al. |
| 4,973,679 | A | * | 11/1990 | Caruthers et al. ......... 536/26.71 |
| 5,026,838 | A | * | 6/1991 | Nojiri et al. ............... 536/25.34 |
| 5,047,524 | A | | 9/1991 | Andrus et al. |
| 5,132,418 | A | * | 7/1992 | Caruthers et al. ......... 536/25.3 |
| RE34,069 | E | * | 9/1992 | Koster et al. ............. 536/25.34 |
| 5,164,491 | A | | 11/1992 | Froehler et al. |
| 5,216,141 | A | * | 6/1993 | Benner .................... 536/27.13 |
| 5,362,866 | A | | 11/1994 | Arnold, Jr. |
| 5,407,795 | A | | 4/1995 | Kolberg et al. |
| 5,510,476 | A | * | 4/1996 | Ravikumar et al. ...... 536/25.31 |
| 5,514,789 | A | | 5/1996 | Kempe |
| 5,548,076 | A | * | 8/1996 | Froehler et al. ......... 536/25.34 |
| 5,554,746 | A | * | 9/1996 | Ravikumar et al. ......... 540/200 |
| 5,614,621 | A | * | 3/1997 | Ravikumar et al. ...... 536/25.34 |
| 5,705,621 | A | * | 1/1998 | Ravikumar ................ 536/23.1 |
| 5,714,597 | A | * | 2/1998 | Ravikumar et al. ...... 536/25.31 |
| 6,096,881 | A | * | 8/2000 | Han et al. ................. 536/25.3 |
| 6,111,086 | A | | 8/2000 | Scaringe |
| 6,465,628 | B1 | * | 10/2002 | Ravikumar et al. ........ 536/23.1 |
| 6,768,005 | B2 | * | 7/2004 | Mellor et al. .............. 536/25.3 |
| 6,858,715 | B2 | * | 2/2005 | Ravikumar et al. ........ 536/23.1 |
| 7,041,816 | B2 | * | 5/2006 | Ravikumar et al. ...... 536/25.31 |
| 2006/0036028 | A1 | * | 2/2006 | Moody et al. ............. 525/54.1 |

FOREIGN PATENT DOCUMENTS

| EP | 0 323 152 A | | 7/1963 |
| EP | 0 288 310 A | | 10/1988 |
| EP | 1 028 124 A2 | | 8/2000 |
| JP | 2003/238586 A2 | * | 8/2003 |
| WO | WO 92/09615 | | 6/1992 |
| WO | WO 94/01446 | | 1/1994 |
| WO | WO 97/40458 | | 10/1997 |
| WO | WO 00/20431 | | 4/2000 |
| WO | WO 00/46231 | | 8/2000 |
| WO | WO 01/27126 A1 | * | 4/2001 |
| WO | WO 01/96358 | | 12/2001 |

OTHER PUBLICATIONS

[R] Ravikumar et al. (VIII), "Efficient Synthesis of Deoxyribonucleotide Phosphorothioates by the Use of DMT Cation Scavenger," Tetrahedron Letters, 36(37), 6587-6590 (Sep. 11, 1995).*
(S) Krotz et al. (I), "Synthesis and Deprotection of β-Silylethyl Protected O, O, O- and O, O, S-Trialkylphosphorothioates," Tetrahedron Letters, 37(12), 1999-2002 (Mar. 18, 1996).*
(T) Krotz et al. (II), "Phosphorothioate Oligonucleotides: Largely Reduced (N-10-Mer and Phosphodiester Content Through the Use of Dimeric Phosphoramidite Synthons," Bioorganic & Medicinal Chemistry Letters, 7(1), 73-78 (Jan. 7, 1997).*

(Continued)

*Primary Examiner*—S. Anna Jiang
*Assistant Examiner*—L. E. Crane
(74) *Attorney, Agent, or Firm*—Pillsbury Winthrop Shaw Pittman LLP

(57) ABSTRACT

A process for the synthesis of phosphorothioate oligonucleotides is provided which comprises assembling an oligonucleotide bound to a solid support in the presence of acetonitrile; prior to cleaving the oligonucleotide from the solid support removing the acetonitrile; and cleaving the oligonucleotide from the solid support. The process is particularly suited to the large scale synthesis of nucleotides. The acetonitrile may be removed from the solid support by one or both of drying and by washing with solvents. Preferred washing solvents comprise trialkylamines.

37 Claims, No Drawings

OTHER PUBLICATIONS (U) Krotz et al. (III), "Phosphorothioates: β-Fragmentation Versus β-Silicon Effect," Angewandte Chemie Intl. Ed., 34(21), 2406-2409 (Nov. 17, 1995).*
(V) Gait, "An Introduction to Modern Methods of DNA Synthesis," Ch. 1 in Oligonucleotide Synthesis—A Practical Approach, Gait (ed.), IRL Press, Washington, DC, 1984, only pp. 1-22 and index/title supplied.*
(W) Sproat et al. (I), "2'-O-Methyloligoribonucleotides: Synthesis and Applications," Ch. 3 in Oligonucleotides and Analogues—A Practical Approach, Eckstein (ed.), IRL Press, New York, NY, 1991, only title and text pp. 49-86 supplied, see especially p. 52.*
(X) Connolly, "Oligonucleotides Containing Modified Bases," Ch. 7 in Oligonucleotides and Analogues—A Practical Approach, Eckstein (ed.), IRL Press, New York, NY, 1991, only title and text pp. 155-183 supplied, see especially p. 157.*
(Y) Conway et al., "Site-Specific Attachment of Labels to the DNA Backbone," Ch. 9 in Olignucleotides and Analogues—A Practical Approach, Eckstein (ed.), IRL Press, New York, NY, 1991, only title and text pp. 211-239 supplied, see especially p. 218.*
(Z) Atkinson et al., "Solid-Phase Synthesis of Oligonucleotides by the Phosphite Triester Method," Ch. 3 in Oligonucleotide Synthesis—A Practical Approach, Gait (ed.), IRL Press, Washington, DC, Jul. 1985, only title and text pp. 35-81 supplied, see especially p. 80.*
(RA) Sproat et al. (II), "Solid-Phase Synthesis of Oligodeoxynucleotides by the Phosphotriester Method," Ch. 4 in Oligonucleotide Synthesis—A Practical Approach, Gait (ed.), IRL Press, Washington, DC, Jul. 1985, only title and text pp. 83-115 supplied, see especially p. 111.*
(SA) Septak, "Kinetic Studies on Depurination and Detritylation of CPG-Bound Intermediates During Olignucleotide Synthesis," Nucleic Acids Research, 24(15), 3053-3058 (1996).*
(TA) Horn et al. (I), "Solid Support Hydrolysis of Apurinic Sites in Synthetic Oligonucleotides for Rapid and Efficient Purification on Reverse-Phase Cartridges," Nucleic Acids Research, 16(24), 11559-11571 (Dec. 23, 1988).*
(UA) Horn et al. (II), "Chemical Synthesis and Characterization of Branched Oligodeoxyribonucleotides (bDNA) for Use as Signal Amplifiers in Nucleic Acid Quantification Assays," Nucleic Acids Research, 25(23), 4842-4849 (Dec. 1, 1997).*
(VA) Horn et al. (III), "The Synthesis of Branched Oligonucleotides as Signal Amplification Multimers for Use in Nucleic Acid Assays," Nucleosides and Nucleotides, 8(5&6), 875-877 (Jul./Sep. 1989).*
(WA) Horn et al. (IV), "Forks and Combs and DNA: The Synthesis of Branched Oligodeoxyribonucleotides," Nucleic Acids Research, 17(17), 6959-6967 (Sep. 12, 1989).*
(XA) Perrin et al., Purification of Laboratory Chemicals, Pergamon Press, New York, NY, 1966, only pp. 54-55, 74-75, 78-79. 82-93, 96-97. 100-101, 108-113, 118-119, 126-133, 138-141, 158-159, 168-169, 178-179, 184-187, 190-191, 198-199, 202-205, 210-211 and 216-217 supplied.*
(YA) Aldrich Catalog/Handbook of Find Chemicals, Aldrich Chemical Company, Milwaukee, WI, 1994-1995, only pp. 1091-1092, 1094, 1096, 1123, 1308, 1313, 1328, 1359-1360, 1371, 1375, 1380, 1384, 1398-1399, 1401, 1403, 1407, 1423, 1461 and 1462 supplied.*
(ZA) Greene et al., Protective Groups in Organic Synthesis, Second Edition, John Wiley & Sons, New York, NY, 1991, only pp. 60-65 supplied.*
(RB) Xu et al., "Use of 1, 2, 4-Dithiazolidine-3, 5-dione (DtsNH) and 3-Ethoxy-1, 2, 4-Dithiazolidine-5-one (EDITH) for Synthesis of Phosphorothioate-Containing Oligodeoxyribonucleotides," Nucleic Acids Research, 24(9), 1602-1607 (1996).*
(SB) Capaldi et al., "Is IT Essential to USe Anhydrous Acetonitrile in the Manufacture of Phosphorothioate Oligonucleotides?" Organic Process Research & Development, 3(6), 485-487 (1999); WEB published Sep. 1, 1999.*
(TB) Oka et al., "An Oxazaphospholidine Approach for the Stereocontrolled Synthesis of Oligonucleoside Phosphorothioates," Journal of the American Chemical Society, 125(27), 8307-8317 (2003; WEB published on Jun. 14, 2003.*

(UB) Krotz et al. (IV), "Phosphorothioate Oligonucleotides with Low Phosphate Diester Content: Greater than 99.9% Sulfurization Efficiency with 'Aged' Solutions of Phenylacetyl Disulfide (PADS)," Organic Process Research & Development, 8(6), 852-858 (2004); WEB published on Oct. 20, 2004.*
Ravikumar et al. (VIII), "Efficient Synthesis of Deoxyribonucleotide Phosphorothioates by the Use of DMT Cation Scavenger," Tetrahedron Letters, 36(37), 6587-6590 (Sep. 11, 1995).*
Krotz et al. (I), "Synthesis and Deprotection of β-Silylethyl Protected O, O, O- and O, O, S-Trialkylphosphorothioates," Tetrahedron Letters, 37(12), 1999-2002 (Mar. 18, 1996).*
Krotz et al. (II), "Phosphorothioate Oligonucleotides: Largely Reduced (N-10-Mer and Phosphodiester Content Through the Use of Dimeric Phosphoramidite Synthons," Bioorganic & Medicinal Chemistry Letters, 7(1), 73-78 (Jan. 7, 1997).*
Krotz et al. (III), "Phosphorothioates: β-Fragmentation Versus β-Silicon Effect," Angewandte Chemie intl. Ed., 34(21), 2406-2409 (Nov. 17, 1995).*
Gait, "An Introduction to Modern Methods of DNA Synthesis," Ch. 1 in Olignucleotide Synthesis—A Practical Approach, Gait (ed.), IRL Press, Washingtn, DC, 1984, only pp. 1-22 and index/title supplied.*
Sproat et al. (I), "2'-O-Methyloligoribonucleotides: Synthesis and Applications," Ch. 3 in Oligonucleotides and Analogues—A Practical Approach, Eckstein (ed.), IRL Press, NY, 1991, only title and text pp. 49-86 supplied, see especially p. 52.*
Connolly, "Oligonucleotides Containing Modified Bases," Ch. 7 in Oligonucleotides and Analogues—A Practical Approach, Eckstein (ed.), IRL Press, New York, NY, 1991, only title and text pp. 155-183 supplied, see especially p. 157.*
Conway et al., "Site-Specific Attachment of Labels to the DNA Backbone," Ch. 9 in Oligonucleotides and Analogues—A Practical Approach, Eckstein (ed.), IRL Press, New York, NY, 1991 title and text pp. 211-239 supplied, see especially p. 218.*
Atkinson et al., "Solid-Phase Synthesis of Oligonucleotides by the Phosphite Triester Method," Ch. 3 in Oligonucleotide Synthesis—A Practical Approach, Gait (ed.), IRL Press, Washington, DC, Jul. 1985, only title and text pp. 35-81 supplied, see especially p. 80.*
Sproat et al. (II), "Solid-Phase Synthesis of Oligodeoxynucleotides by the Phosphotriester Method," Ch. 4 in Oligonucleotide Synthesis— A Practical Approach, Gait (ed.), IRL Press Washington, DC, Jul. 1985, only title and text pp. 83-115 supplied, see especially p. 111.*
Septak, "Kinetic Studies on Depurination and Detritylation of CPG-Bound Intermediates During Olignucleotide Synthesis," Nucleic Acids Research, 24(15), 3053-3058 (1996).*
Horn et al. (I), "Solid Support Hydrolysis of Apurinic Sites in Synthetic Oligonucleotides for Rapid and Efficient Purification on Reverse-Phase Cartridges," Nucleic Acids Research, 16(24), 11559-11571 (Dec. 23, 1988).*
Horn et al. (II), "Chemical Synthesis and Characterization of Branched Oligodeoxyribonucleotides (bDNA) for Use as Signal Amplifiers in Nucleic Acid Quantification Assay" Nucleic Acids Research, 25(23), 4842-4849 (Dec. 1, 1997).*
Horn et al. (III), "The Synthesis of Branched Oligonucleotides as Signal Amplification Multimers for Use in Nucleic Acid Assay" Nucleosides and Nucleotides, 8(5&6), 875-877 (Jul./Sep. 1989).*
Horn et al. (IV), "Forks and Combs and DNA: The Synthesis of Branched Oligodeoxyribonucleotides," Nucleic Acids Research, 17(17), 6959-6967 (Sep. 12, 1989).*
Perrin et al., Purification of Laboratory Chemicals, Pergamon Press, New York, NY, 1966, only pp. 54-55, 74-75, 78-79. 82-93, 96-97. 100-101, 108-113, 118-119, 126-133, 138-141, 158-159, 168-169, 178-179, 184-187, 190-191, 198-199, 202-205, 210-211 and 216-217 supplied.*
Aldrich Catalog/Handbook of Fine Chemicals, Aldrich Chemical Company, Milwaukee, WI, 1994-1995, only pp. 1091-1092, 1094, 1096, 1123, 1308, 1313, 1328, 1359-1360, 1371, 1375, 1380, 1384, 1398-1399, 1401, 1403, 1407, 1423, 1461 and 1462 supplied.*
Greene et al., Protective Groups in Organic Synthesis, Second Edition, John Wiley & Sons, New York, NY, 1991, only pp. 60-65 supplied.*

Xu et al., "Use of 1, 2, 4-Dithiazolidine-3, 5-dione (DtsNH) and 3-Ethoxy-1, 2, 4-Dithiazolidine-5-one (EDITH) for Synthesis of Phosphorothioate-Containing Oligodeoxyribonucleotides," *Nucleic Acids Research*, 24(9), 1602-1607 (1996).*

Capaldi et al., "Is IT Essential to USe Anhydrous Acetonitrile in the Manufacture of Phosphorothioate Oligonucleotides?" *Organic Process Research & Development*, 3(6), 485-487 (1999); WEB published Sep. 1, 1999.*

Oka et al., "An Oxazaphospholidine Approach for the Stereocontrolled Synthesis of Oligonucleoside Phosphorothioates," *Journal of the American Chemical Society*, 125(27), 8307-8317 (2003; WEB published on Jun. 14, 2003.*

Krotz et al. (IV), "Phosphorothioate Oligonucleotides with Low Phosphate Diester Content: Greater than 99.9% Sulfurization Efficiency with 'Aged' Solutions of Phenylacetyl Disulfide (PADS)," *Organic Process Research & Development*, 8(6), 852-858 (2004); WEB published on Oct. 20, 2004.*

Chemical Abstracts, vol. 19, No. 25 (1979) Abstract No. 211802—Arshady et al. "Easily prepared polar support for solid phase peptide and oligonucleotide synthesis" *J. Chem. Soc.*, pp. 423-425, Chemical Communications, 1979, Issue No. 9.

* cited by examiner

PROCESS FOR THE PREPARATION OF PHOSPHOROTHIOATE OLIGONUCLEOTIDES

CROSS REFERENCE TO RELATED APPLICATIONS

This application is a continuation-in-part of International Application No. PCT/GB01/05338, filed Dec. 3, 2001, which further claims priority from U.S. Ser. No. 09/740,031, filed Dec. 20, 2000, now U.S. Pat. No. 6,768,005. These applications, in their entirety, are incorporated herein by reference.

SUMMARY OF THE INVENTION

The present invention concerns a method for the synthesis of phosphorothioate oligonucleotides.

BACKGROUND OF THE INVENTION

In the past 15 years or so, enormous progress has been made in the development of the synthesis of oligodeoxyribonucleotides (DNA sequences), oligoribonucleotides (RNA sequences) and their analogues 'Methods in Molecular Biology, Vol. 20, Protocol for Oligonucleotides and Analogs', Agrawal, S. Ed., Humana Press, Totowa, 1993. Much of the work has been carried out on a micromolar or even smaller scale, and automated solid phase synthesis involving monomeric phosphoramidite building blocks Beaucage, S. L.; Caruthers, M. H. *Tetrahedron Lett.*, 1981, 22, 1859–1862 has proved to be the most convenient approach. Indeed, high molecular weight DNA and relatively high molecular weight RNA sequences can now be prepared routinely with commercially available synthesisers. These synthetic oligonucleotides have met a number of crucial needs in biology and biotechnology.

Whereas milligram quantities have generally sufficed for molecular biological purposes, gram to greater than 100 gram quantities are required for clinical trials. Several oligonucleotide analogues that are potential antisense drugs are now in advanced clinical trials. If, as seems likely in the very near future, one of these sequences becomes approved, say, for the treatment of AIDS or a form of cancer, kilogram, multikilogram or even larger quantities of a specific sequence or sequences will be required.

Many of the oligonucleotides currently of interest in the phamaceutical industry are analogues of natural oligonucleotides which comprise phosphorothioated-internucleoside linkages. When phosphorothioate linkages are present, particularly when such linkages comprise a major proportion of the linkages, and especially when they comprise 100% of the internucleoside linkages, it is highly desirable that the concentration of impurity, non-phosphorothioated linkages in the final product is kept to a pharmacologically acceptable level.

A large number of protocols for the synthesis of oligonucleotides employ acetonitrile as a solvent for the reagents employed. Acetonitrile is attractive as a solvent because it is inert towards the reagents and oligonucleotide product, it has good solvation properties and is environmentally acceptable. Commonly, for large-scale syntheses, a high concentration of acetonitrile is present during the stage when the oligonucleotide product is cleaved from the solid support. Hitherto, this has been acceptable for large scale synthesis because of the perceived inert nature of acetonitrile. However, during the course of the studies resulting in the present invention, it has now been surprisingly found that higher purity oligonucleotides can be obtained by reducing the concentration of acetonitrile present during the cleavage stage.

DETAILED DESCRIPTION OF THE INVENTION

According to one aspect of the present invention, there is provided a process for the large-scale synthesis of phosphorothioate oligonucleotides which comprises:
  a) assembling an oligonucleotide bound to a solid support in the presence of acetonitrile; and
  b) cleaving the oligonucleotide from the solid support;

characterised in that the concentration of acetonitrile is reduced to less than 10% by weight of the oligonucleotide plus solid support prior to the cleavage of the oligonucleotide from the solid support.

The phosphorothioate oligonucleotides can be assembled by known techniques for solid phase synthesis, for example using H-phosphonate or particularly phosphoramidite chemistry. For the phosphoramidite approach, commonly, the sequence employed is: deprotection of the nucleoside bound to solid support, preferably at the 5'-position; coupling of a, preferably 3'-,phosphoramidite nucleoside to form a supported oligonucleotide; sulphurisation of the supported oligonucleotide by reaction with a sulphurising agent to produce a supported phosphorothioate oligonucleotide; and capping of unreacted supported nucleoside with a capping reagent. This cycle is then repeated as often as is necessary to assemble the desired sequence of the oligonucleotide. When a mixed phosphate/phosphorothioate product is desired, the sulphurisation stage can be replaced with an oxidation step to produce a phosphate linkage at the desired location. On completion of the assembly, and prior to cleavage from the support, the supported oligonucleotide is commonly washed with acetonitrile in order to remove traces of unreacted reagents.

Acetonitrile can be removed by drying of the supported oligoncleotide, optionally under reduced pressure. The acetonitrile is commonly removed at ambient temperature, for example from 15 to 30° C., although elevated temperatures, such as from 30 to 80° C., for example from 40 to 60° C., may be employed.

The process according to the first aspect of the present invention is employed for large scale synthesis of oligonucleotides. Large scale synthesis of oligonucleotides is often regarded as being at or above a batch size of 10 mmol oligonucleotide, commonly at or above 15 mmol, often at or above 25 mmol, for example greater than 50 mmol, and especially greater than 75 mmol of oligonucleotide. In many embodiments, the process of the present invention is employed for oligonucleotide synthesis at a scale in the range of from 100–500 mmol.

On completion of the assembly of the desired product, the product may be cleaved from the solid support. Cleavage methods employed are those known in the art for the given solid support. When the product is bound to the solid support via a cleavable linker, cleavage methods appropriate for the linker are employed, for example, contact with methylamine, aqueous methylamine solution, liquified ammonia, gaseous ammonia and particularly contact with concentrated aqueous ammonia solution. Following cleavage, the product can be purified using techniques known in the art, such as one or more of ion-exchange chromatography, reverse phase chromatography, and precipitation from an appropriate solvent. Further processing of the product by for example ultrafiltration may also be employed.

Solid supports that are employed in the process according to the present invention are substantially insoluble in the solvent employed, and include those supports well known in the art for the solid phase synthesis of oligonucleotides. Examples include silica, controlled pore glass, polystyrene, copolymers comprising polystyrene such as polystyrene-poly(ethylene glycol) copolymers and polymers such as polyvinylacetate. Additionally, microporous or soft gel supports, especially poly(acrylamide) supports, such as those more commonly employed for the solid phase synthesis of peptides may be employed if desired. Preferred poly(acrylamide) supports are amine-functionalised supports, especially those derived from supports prepared by copolymerisation of acryloyl-sarcosine methyl ester, N,N-dimethylacrylamide and bis-acryloylethylenediamine, such as the commercially available (Polymer Laboratories) support sold under the catalogue name PL-DMA. The procedure for preparation of the supports has been described by Atherton, E.; Sheppard, R. C.; in *Solid Phase Synthesis: A Practical Approach*, Publ., IRL Press at Oxford University Press (1984). The functional group on such supports is a methyl ester and this is initially converted to a primary amine functionality by reaction with an alkyl diamine, such as ethylene diamine.

According to a second aspect of the present invention, there is provided a process for the synthesis of phosphorothioate oligonucleotides which comprises:

a) assembling an oligonucleotide bound to a solid support in the presence of acetonitrile;

b) prior to cleaving the oligonucleotide from the solid support, washing the oligonucleotide bound to a solid support with a washing regime employing one or more solvent washes; and c) cleaving the oligonucleotide from the solid support;

characterised in that the final wash of the washing regime employs a solvent other than acetonitrile or dioxane.

The washing regime employs one or more solvent washes. When the washing regime comprises a single wash, the solvent employed is free from acetonitrile and dioxane. When more than one solvent wash is employed, acetonitrile and dioxane may be employed in the wash stages other than the final wash. However, it is preferred that acetonitrile and dioxane are not employed in any stage of the washing regime.

Solvents which can be employed are preferably inert solvents which do not degrade the oligonucleotide under the conditions under which the solvent is employed. Examples of inert solvents that can be employed include inert organic solvents and inert aqueous solvents.

Preferably, the washing with solvent is effected such that the concentration of acetonitrile is reduced to less than 10% by weight of the oligonucleotide plus solid support.

Organic solvents which can be employed include aromatic hydrocarbons, for example toluene; aliphatic hydrocarbons, for example cyclohexane; haloalkanes, particularly dichloromethane; esters, particularly alkyl esters such as ethyl acetate and methyl or ethyl propionate; alcohols, particularly aliphatic alcohols such as $C_{1-4}$ alkyl alcohols, for example methanol, ethanol or isopropanol; amides, such as dimethylformamide and N-methylpyrollidinone; basic, nucleophilic solvents such as pyridine or alkylamines, especially tri(alkyl), such as tri($C_{1-4}$-alkyl)amines; polar ethers such as tetrahydrofuran; and sulphoxides, for example dimethylsulphoxide.

Aqueous solvents that can be employed include water, aqueous buffer solutions, mixtures of water and water miscible inert organic solvents, especially those solvents described above.

Solid supports that may be employed are those described with the respect to the first aspect of the present invention. In many embodiments, it may be preferred to employ an organic solvent when the support is hydrophobic, such as poly(styrene). In other embodiments, it may be preferred to employ an aqueous solvent when the support is hydrophilic, such as controlled pore glass or silica. In further embodiments, when the support is microporous, it may be preferred to employ a solvent which swells the support.

In certain preferred embodiments, the solvent employed serves to remove protecting groups from the oligonucleotide, particularly betacyanoethyl protecting groups from the internucleotide linkages, and nucleobase protecting groups. Preferred solvents are alkylamines, especially tri(alkyl)amines, such as tri($C_{1-4}$-alkyl)amines, and most preferably triethylamine.

The processes according to the second aspect of the present invention can be employed in both small (ie<25 mmol scale) and large scale oligonucleotide synthesis as described above in respect of the first aspect of the present invention.

The oligonucleotides can be assembled, and after washing, cleaved from the solid support, by the methods described above in respect of the first aspect of the present invention.

In both the first and second aspects of the present invention, the acetonitrile concentration is preferably reduced to less than 5%, often less than 3%, particularly less than about 2%, and especially less than about 1%, by weight of the oligonucleotide plus solid support.

An especially preferred embodiment of the present invention comprises assembling an oligonucleotide bound to a solid support in the presence of acetonitrile, air drying the supported oligonucleotide, contacting the dried supported oligonucleotide with a trialkylamine, preferably triethylamine, for sufficient time to deprotect the oligonucleotide, and subsequently cleaving the oligonucleotide from the solid support.

In a related embodiment of the present invention, there is provided a process for the synthesis of phosphorothioate oligonucleotides which comprises:

a) assembling an oligonucleotide bound to a solid support in the presence of acetonitrile;

b) prior to cleaving the oligonucleotide from the solid support, washing the oligonucleotide bound to a solid support with a washing regime employing one or more solvent washes; and c) cleaving the oligonucleotide from the solid support;

characterised in that the final wash of the washing regime employs as solvent wash a solution comprising an alkylamine, preferably a tri($C_{1-4}$)alkylamine such as triethylamine, substantially free from acetonitrile. One or more solvent washes may be employed. It is preferred that acetonitrile is not employed in any of the solvent washes.

The synthesis of oligonucleotides using phosphoramidite chemistry wherein the oilgonucleotide is synthesised supported on a microporous support is believed to be novel. Accordingly, in a third aspect of the present invention, there is provided a process for the preparation of an oligonucleotide which comprises coupling a nucleoside or oligonucleotide phosphoramidite with a nucleoside or oligonucleotide comprising a free hydroxy group supported on a solid support to form an oligonucleotide phosphite triester, characterised in that the solid support is a microporous support.

Microporous supports are preferably poly(acrylamide) supports, such as those more commonly employed for the solid phase synthesis of peptides, may be employed if desired. Preferred poly(acrylamide) supports are amine-functionalised supports, especially those derived from supports prepared by copolymerisation of acryloyl-sarcosine methyl ester, N,N-dimethylacrylamide and bis-acryloylethylenediamine, such as the commercially available (Polymer Laboratories) support sold under the catalogue name PL-DMA. The procedure for preparation of the supports has been described by Atherton, E.; Sheppard, R. C.; in *Solid Phase Synthesis: A Practical Approach*, Publ., IRL Press at Oxford University Press (1984), the microporous supports of which are incorporated herein by reference. The functional group on amine-functionalised supports is a methyl ester and this is initially converted to a primary amine functionality by reaction with an alkyl diamine, such as ethylene diamine. The microporous supports are preferably employed in the form of polymeric beads.

The process according to the third aspect of the present invention is preferably carried out in the presence of a solvent which swells the microporous support. Examples of such solvents include haloalkanes, particularly dichloromethane; esters, particularly alkyl esters such as ethyl acetate and methyl or ethyl propionate; ethers such as tetrahydrofuran; and preferably amides, such as dimethylformamide and N-methylpyrollidinone. The most preferred solvent is dimethylformamide.

The nucleoside or oligonucleotide phosphoramidite employed can comprise a 3'- or 5'-phosphoramidite group, most preferably a 3'-phosphoramidite group. Commonly, the phosphoramidite is a betacyanoethyloxy phosphoramidite. The nucleoside or oligonucleotide phosphoramidite commonly comprises a protected hydroxy group at whichever of the 3'- or 5'-positions is not a phosphoramidite. Preferably, at the 5'-position is a protected hydroxy group. Preferred protecting groups are pixyl and trityl, especially dimethoxytrityl, groups.

The nucleoside or oligonucleotide comprising a free hydroxy group employed can comprise a 3'- or 5'-hydroxy group, and is commonly bound to the solid support via whichever of the 3'- or 5' positions is not free hydroxy. Most preferably, the nucleoside or oligonucleotide comprising a free hydroxy group is bound to the solid support via the 3'-position, and comprises a free 5' hydroxy group.

The nucleoside or oligonucleotide comprising a free hydroxy group is commonly bound to the solid support via a cleavable linker.

The coupling of the nucleoside or oligonucleotide phosphoramidite with a nucleoside or oligonucleotide comprising a free hydroxy group takes place in the presence of a suitable activator. Examples of such activators are those known in the art for conventional phosphoramidite oligonucleotide synthesis, and include tetrazole, thioethyltetrazole, nitrophenyltetrazole and dicyanoimidazole. Commonly, the nucleoside or oligonucleotide phosphoramidite is employed as a solution in the solvent employed to swell the microporous support. Advantageously, the phosphoramidite solution is mixed with the swollen support comprising the free hydroxy group prior to addition of the activator as a solution in the solvent employed to swell the microporous support.

The oligonucleotide phosphite triester produced in the process of the third aspect of the present invention is commonly oxidised or sulphurised to form an oligonucleotide phosphate or phosphorothioate. Oxidising agents employed are those known in the art for conventional phosphoramidite oligonucleotide synthesis, and include iodine and t-butylhydroperoxide. Sulphurising agents employed are those known in the art for conventional phosphoramidite oligonucleotide synthesis, and include xanthane hydride, phenylacetyl disulphide and Beaucage reagent. The oxidising or sulphurising agents are commonly employed as a solution in the solvent employed to swell the microporous support.

A capping treatment, employing capping agents known in the art, for example a mixture of pyridine and acetic anhydride and a mixture of pyridine and N-methylimidazole, may be employed. Advantageously, the capping agents are employed in the presence of the solvent employed to swell the microporous support.

Pixyl or trityl protecting groups present in the oligonucleotide phosphate or phosphorothioate bound to the solid support, commonly at the 5'-position, can be removed by conventional detritylation techniques, for example by treatment with a solution of dichloroacetic acid. Preferably, the dichloroacetic acid is employed as a solution in the solvent employed to swell the microporous support, for example dichloromethane or advantageously and amide, particularly dimethylformamide or N-methylpyrrolidinone. Removal of the pixyl or trityl protecting groups produces a free hydroxyl group which can then be employed for further coupling. Further couplings can be carried out in order to assemble the desired sequence. On completion of the assembly of the desired sequence, the product can be cleaved from the solid support using techniques appropriate to the linker employed.

The processes according to the present invention can be employed to synthesise phosphorothioated deoxyribonucleotides and ribonucleotides. The nucleotides may comprise bases, protecting groups and other modifications known in the nucleotide art. For example, bases which may be present include purines and pyrimidines, commonly A, G, T, C and U. Other bases which may be present include hypoxanthine, inosine and 2,6-diaminopurine. Protecting groups which may be present include base-protecting groups, such as benzyl, acetyl, phenoxyacetyl and isobutyryl groups, and hydroxy-protecting groups, such as pixyl and trityl, especially dimethoxytrityl, groups. Ribonucleotides may be modified at the 2'-position by an alkoxy or alkoxyalkyl substituent, such as a methoxy or methoxyethoxy substituent or may be protected at the 2'-position by a hydroxy protecting group such as tertiary butyldimethylsilyl, 1-(2-fluorophenyl)-4-methoxypiperidine-4-yl (Fpmp) or 1-(2-chlorophenyl)-4-methoxypiperidine-4-yl (Cpmp). Other modifications, including inverted nucleosides, abasic nucleosides and L-nucleosides may also be present. Deoxyribonucleotides may be modified at the 2'-position by a 2'-C-alkyl group. Chimeric nucleotides, including mixed deoxyribonucleotides and ribonucleotides, and/or mixed phosphate/phosphorothioate nucleotides can be prepared.

In many embodiments, the processes of the present invention are employed to prepare oligonucleotides having from 1 to 100, often from 5 to 75, preferably from 8 to 50 and particularly preferably from 10 to 30 internucleoside linkages. Commonly, the processes of the present invention are employed to prepare compounds wherein at least 50% of the internucleoside linkages are phosphorothioated, preferably at least 75%, and most preferably 90 to 100% phosphorothioated.

Examples of cleavable linkers that may be employed in the processes of the present invention include those well known in the art for the solid phase synthesis of oligonucleotides, such as urethane, oxalyl, succinyl, and amino-derived linkers. Succinyl linkers are preferred.

The invention will now be illustrated without limitation by the following examples.

EXAMPLES 1–3 AND COMPARISON A

A sample of a fully phosphorothioated deoxyribonucleotide comprising 17 phosphorothioate groups was prepared using standard phosphoramidite chemistry. The product was produced trityl-on on a polystyrene support. After completion of the assembly and sulphurisaton, the supported nucleotide was washed with acetonitrile.

Three samples of the supported oligonucleotide were treated as follows. For Example 1, the supported oligonucleotide was air dried on a filter funnel. For Example 2, the sample was washed with triethylamine. For Example 3, the sample was washed with 2.5M aqueous sodium acetate solution. In each of Examples 2 and 3, the washing took place on a filter funnel under slightly reduced pressure, but operated so as to minimise evaporation of acetonitrile. The acetonitrile contents (% w/w) of the samples were measured by GC. The products of Examples 1 to 3 were cleaved using standard ammonolysis conditions using concentrated aqueous ammonia to obtain the oligonucleotide product. For Comparison A, a further sample of the supported oligonucleotide was cleaved under the same conditions, but without a drying or washing treatment. In each case, the weight percentage of P=O impurity in the samples was determined using Ion exchange chromatography. The results are given in Table 1 below.

TABLE 1

| SAMPLE | Acetonitrile Content | % P=O |
|---|---|---|
| Comparison A | 33% | 9% |
| Example 1 | <1% | 5% |
| Example 2 | 1% | 5% |
| Example 3 | 9% | 5% |

The results given in Table 1 show that the oligonucleotide produced by the processes of the present invention (Examples 1 to 3) gave significantly purer oligonucleotide products than the comparative process wherein the concentration of acetonitrile was not reduced prior to cleavage.

EXAMPLE 4

Synthesis of Oligonucleotide Using a Microporous Support

The following reaction was carried out under a nitrogen atmosphere. To a 40 ml solid phase glass sinter/bubbler reactor of the type commonly employed in peptide synthesis, containing 1 g of amine functionalised poly(acrylamide) resin (loading 1 mmol/g) obtained from Polymer Laboratories under the trade name PL-DMA, was added 3 equivalents of 5'-DMT-T-3'-succinate. Sufficient N-methylpyrrolidinone (NMP) was added to make the resin just mobile to nitrogen agitation, followed by 4 equivalents of diisopropylcarbodiimide and 3 equivalents of diisopropylethylamine. The mixture was agitated with nitrogen until loading of the resin was complete as shown by the Kaiser test. The resin was washed with NMP (5× bed volume) and dichloromethane (DCM, 5× bed volume). 10 equivalents of pyrrole was added to the DCM wet resin followed by a 15% v/v solution of dichloroacetic acid (DCA) in DCM (2× bed volume). The mixture was agitated with nitrogen for 1 hour and then washed with DCM (5× bed volume) and NMP (5× bed volume) to form a 5'-deprotected 3'-supported T.

Three equivalents of 5'-DMT-T-3'-(betacyanoethyloxydiisopropyl-amino)phosphoramidite was added to the supported T prepared above. Sufficient NMP was added to make the resin just mobile to nitrogen agitation, followed by 3.3 equivalents of S-ethyltetrazole. The mixture was agitated with nitrogen for 30 minutes, and then washed with NMP (10× bed volume). Sulfurisation was achieved using Beaucage reagent (5 equivalents) for 60 minutes in the presence of sufficient NMP to make the resin just mobile to nitrogen agitation. The resin was washed with NMP (5× bed volume) and DCM (5× bed volume) to form a 5'-DMT protected supported dimer phosphorothioate. The detritylation, coupling and sulfuristaion cycles were repeated 2 further times to form a 5'-DMT supported tetramer phosphorothioate. This was detritylated using the using the conditions given above. Cleavage from the solid support, and removal of betacyanoethyl groups was achieved by treatment with concentrated aqueous ammonia solution for 48 hours at room temperature.

What is claimed is:

1. In an improved process for the large-scale synthesis of phosphorothioate oligonucleotides comprising:
   a) assembling by phosphoramidite chemistry a phosphorothioate oligonucleotide bound to a solid support in the presence of acetonitrile;
   b) reduction of the content of acetonitrile in the solid support; and
   c) cleaving the oligonucleotide from the solid support; wherein the improved process reduces the concentration of acetonitrile to less than 10% by weight of the oligonucleotide plus solid support.

2. The improved process according to claim 1, wherein the process reduces the concentration of acetonitrile to less than 5% by weight of the oligonucleotide plus solid support.

3. The improved process according to claim 2, wherein the process reduces the concentration of acetonitrile to less than 1% by weight of the oligonucleotide plus solid support.

4. The improved process according to claim 1, which is operated at or above a batch size of 10 mmol of oligonucleotide.

5. The improved process according to claim 1, wherein the oligonucleotide is bound to the solid support via a cleavable linker selected from the group consisting of an urethanyl linker an oxalyl linker and a succinyl linkes 6. The improved process according to claim 1 wherein the oligonucleotide is cleaved from the solid support by contact with a cleaving reagent, said cleavage reagent comprising methylamine, aqueous methylamine solution, liquified ammonia, gaseous ammonia or concentrated aqueous ammonia solution.

7. The improved process according to claim 1 which is employed to prepare oligonucleotides having from 1 to 100 internucleoside linkages.

8. The improved process according to claim 7, which is employed to prepare compounds wherein at least 50% of the internucleoside linkages are phosphorothioate linkages.

9. The improved process according to claim 8, wherein 90 to 100% of the internucleoside linkages are phosphorothioate linkages.

10. An improved process for the synthesis of phosphorothioate nucleotides comprising:
   a) assembling by phosphoramidite chemistry a phosphorothoate oligonucleotide bound to a solid support in the presence of acetonitrile;

b) prior to cleaving the oligonucleotide from the solid support, washing the oligonucleotide bound to the solid support with a washing regime employing one or more solvent washes to reduce the acetonitrile concentration, wherein the final wash of the washing regime employs a solvent selected from the group consisting of aromatic hydrocarbons, aliphatic hydrocarbons, haloalkanes, esters, alcohols, amides, pyridine, alkylamines, polar ethers, sulphoxides, water, aqueous buffer solutions and mixtures of water and water miscible esters, alcohols, amides, pyridine, alkylamines, polar ethers or sulphoxides; and c) cleaving the oligonucleotide from the solid support.

11. The process according to claim 10, wherein the solvent employed in the final wash of the washing regime is selected from the group consisting of toluene, cyclohexane, dichloromethane, ethyl acetate, methyl propionate, ethyl propionate, $C_{1-4}$ alkyl alcohols, dimethylformamide N-methylpyrrolidinone, tri($C_{1-4}$-alkyl)amines, tetrahydrofuran, dimethylsulphoxide and aqueous sodium acetate solution.

12. The process according to claim 11, wherein the solvent is triethylamine.

13. The process according to claim 10, wherein the oligonucleotide is bound to the solid support via a cleavable linker selected from the group consisting of a urethanyl linker an oxalyl linker, and a succinyl linker.

14. The process according to claim 13, wherein the oligonucleotide is cleaved from the solid support by contact with a cleaving reagent, said cleaving reagent comprising methylamine, aqueous methylamine solution, liquified ammonia, gaseous ammonia or concentrated aqueous ammonia solution.

15. The process according to claim 10, which is employed to prepare oligonucleotides having from 1 to 100 internucleoside linkages.

16. The process according to claim 15, which is employed to prepare compounds wherein at least 50% of the internucleoside linkages are phosphorothioate linkages.

17. The process according to claim 16, wherein 90 to 100% of the internucleoside linkages are phosphorothioate linkages.

18. An improved process for the synthesis of phosphorothioate nucleotides comprising:

a) assembling by phosphoramidite chemistry a phosphorothoate oligonucleotide bound to a solid support in the presence of acetonitrile;

b) prior to cleaving the oligonucleotide from the solid support, washing the oligonucleotide bound to the solid support with a washing regime employing one or more solvent washes to reduce the acetonitrile concentration, wherein the final wash of the washing regime employs as solvent a solution comprising a trialkylamine; and c) cleaving the oligonucleotide from the solid support.

19. The process according to claim 18, wherein the solvent is triethylamine.

20. An improved process for the synthesis of phosphorothioate nucleotides comprising assembling by phosphoramidite chemistry a phosphorothoate oligonucleotide bound to a solid support in the presence of acetonitrile; air drying the supported oligonucleotide for sufficient time to reduce the concentration of acetonitrile; contacting the dried supported oligonucleotide with a trialkylamine for sufficient time to deprotect the the oligonucleotide, and subsequently cleaving the oligonucleotide from the solid support.

21. The process according to claim 20, wherein the process reduces the concentration of acetonitrile to less than 5% by weight of the oligonucleotide plus solid support.

22. The process according to claim 21, wherein the process reduces the concentration of acetonitrile to less than 1% by weight of the oligonucleotide plus solid support.

23. The process according to claim 20, wherein the oligonucleotide is bound to the solid support via a cleavable linker selected from the group consisting of a urethanyl linker an oxalyl linker, and a succinyl linker.

24. The process according to claim 23, wherein the oligonucleotide is cleaved from the solid support by contact with acleaving reagent, said cleavage reagent comprising methylamine, aqueous methylamine solution, liquified ammonia, gaseous ammonia or concentrated aqueous ammonia solution.

25. The process according to claim 20, which is employed to prepare oligonucleotides having from 1 to 100 internucleoside linkages.

26. The process according to claim 25, which is employed to prepare compounds wherein at least 50% of the internucleoside linkages are phosphorothioate linkages.

27. The process according to claim 26, wherein 90 to 100% of the internucleoside linkages are phosphorothioate linkages.

28. The process according to claim 9, wherein the process reduces the concentration of acetonitrile to less than 1% by weight of the oligonucleotide plus solid support, and which is operated at or above a batch size of 10 mmol of oligonucleotide.

29. The process according to claim 17, wherein the process reduces the concentration of acetonitrile to less than 1% by weight of the oligonucleotide plus solid support, and which is operated at or above a batch size of 10 mmol of oligonucleotide.

30. The process according to claim 27, wherein the process reduces the concentration of acetonitrile to less than 1% by weight of the oligonucleotide plus solid support, and which is operated at or above a batch size of 10 mmol of oligonucleotide.

31. The improved process according to claim 1, wherein the phosphoramidite chemistry comprises the reaction of betacyanoethyloxy phosphoramidites.

32. The process according to claim 10, wherein the phosphoramidite chemistry comprises the reaction of betacyanoethyloxy phosphoramidites.

33. The process according to claim 18, wherein the phosphoramidite chemistry comprises the reaction of betacyanoethyloxy phosphoramidites.

34. The process according to claim 28, wherein the phosphoramidite chemistry comprises the reaction of betacyanoethyloxy phosphoramidites.

35. The process according to claim 29, wherein the phosphoramidite chemistry comprises the use of betacyanoethyloxy phosphoramidites.

36. The process according to claim 30, wherein the phosphoramidite chemistry comprises the reaction of betacyanoethyloxy phosphoramidites.

37. The process according to claim 20, wherein the trialkylamine is triethylamine.

* * * * *